United States Patent [19]

Singer et al.

[11] 4,237,019

[45] Dec. 2, 1980

[54] 1-THIOCYANATO-8-SUBSTITUTED NAPHTHALENE COMPOUNDS AND THEIR USE AS BIOCIDES

[75] Inventors: Michael Singer; Bernard Tury, both of Manchester, England

[73] Assignee: Imperial Chemical Industries Limited, London, England

[21] Appl. No.: 968,433

[22] Filed: Dec. 8, 1978

[30] Foreign Application Priority Data

Dec. 23, 1977 [GB] United Kingdom ............... 53749/77

[51] Int. Cl.$^3$ .................. C10M 1/20; C10M 1/30; C10M 1/38; C10M 1/32
[52] U.S. Cl. .................. 252/47.5; 252/49.3; 252/49.5; 260/29.6 H; 260/454
[58] Field of Search .................. 252/47.5, 49.3, 49.5; 260/29.6 H, 454

[56] References Cited

U.S. PATENT DOCUMENTS

| 1,765,678 | 6/1930 | Kaufmann et al. | 260/454 |
|---|---|---|---|
| 1,790,097 | 1/1931 | Kaufmann et al. | 260/454 |
| 2,122,781 | 7/1938 | Salzberg | 260/454 X |
| 3,255,077 | 6/1966 | Shipman et al. | 167/32 |
| 3,483,244 | 12/1969 | Reifschneider et al. | 260/454 |
| 3,535,362 | 10/1970 | Ottmann et al. | 260/454 |
| 3,637,787 | 1/1972 | Rasschaert et al. | 260/454 |

FOREIGN PATENT DOCUMENTS 1159507  7/1969  United Kingdom .

OTHER PUBLICATIONS

Chem. Abs. 59 11383b (1963).

*Primary Examiner*—W. J. Shine
*Attorney, Agent, or Firm*—Cushman, Darby & Cushman

[57] ABSTRACT

1-Thiocyanato-8-substituted naphthalene compounds and their use as biocides, especially for protecting aqueous media against infection by micro-organisms.

12 Claims, No Drawings

1-THIOCYANATO-8-SUBSTITUTED NAPHTHALENE COMPOUNDS AND THEIR USE AS BIOCIDES

This invention relates to certain naphthalene derivatives and their use as biocides.

Many media, and in particular aqueous media, are susceptible to attack by micro-organisms. Such media include the cooling water systems of power stations, the water systems of paper mills, aqueous oil emulsions such as the cutting oils used as lubricants and coolants in the machining of metals, water-based paints and adhesives, and paint films.

Numerous compounds having diverse chemical structures have been proposed for the elimination and/or control of micro-organisms in a wide variety of different media, and these compounds are effective to a greater or lesser extent. The compounds of the present invention are very effective biocides against a wide spectrum of micro-organisms.

According to the present invention there are provided 1-thiocyanato-8-substituted naphthalene compounds of the formula:

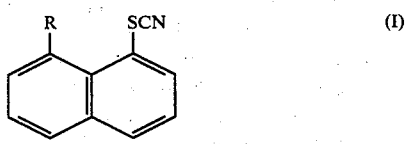

where R is optionally substituted alkyl, optionally substituted alkoxy, optionally substituted aryloxy, hydroxyl, halogen, nitro, optionally substituted aryl, cyano, sulphonic acid, primary, secondary or tertiary amino, optionally substituted carbamoyl or optionally substituted sulphamoyl, and wherein the naphthalene nucleus may carry other substituents and may form part of a larger fused ring system.

The alkyl groups represented by R are preferably lower alkyl groups, and may carry substituents such as hydroxy, alkoxy or halogen. Examples of such alkyl and substituted alkyl groups are methyl, ethyl, n-propyl, isopropyl, n-butyl, 2-hydroxyethyl, 2-chloroethyl and 2-methoxyethyl.

The aryl groups represented by R are preferably phenyl, which may be substituted by alkyl, alkoxy, nitro or halogen. Examples of such substituted phenyl radicals are o-, m- and p-tolyl, o-, m- and p-methoxyphenyl, o-, m- and p-chloro- (or bromo-) phenyl and o-, m- and p-nitrophenyl. The alkoxy groups represented by R are preferably lower alkoxy groups, for example, methoxy and ethoxy.

The aryloxy groups represented by R are preferably phenoxy groups, which may be substituted by alkyl, alkoxy, nitro or halogen.

Examples of secondary and tertiary amino groups represented by R are methylamino, dimethylamino, ethylamino, diethylamino and phenylamino.

The substituted carbamoyl or sulphamoyl groups represented by R are preferably of the formula -CONR¹R² or -SO₂NR¹R² wherein one of R¹ and R² is hydrogen and the other is lower alkyl, or R¹ and R² are each independently lower alkyl, or R¹ and R² together may form a five or six-membered heterocyclic ring including the nitrogen atom and which may include other hetero atoms. Examples of substituted carbamoyl or sulphamoyl groups are N-methylcarbamoyl, N,N-dimethylcarbamoyl, N-methylsulphamoyl, N,N-dimethylsulphamoyl, piperidinocarbonyl, piperidinosulphonyl, morpholinocarbonyl, morpholinosulphonyl, N-phenylcarbamoyl and N-phenylsulphamoyl.

Examples of the optional substituents which may be present on the naphthalene nucleus are lower alkyl, lower alkoxy, hydroxy, halogen, nitro, optionally substituted amino, sulphonic acid, optionally substituted sulphamoyl and thiocyanato.

When halogen atoms are present in any of the compounds according to the present invention, it is preferred that they are chlorine or bromine atoms.

The terms "lower alkyl" and "lower alkoxy" in this specification mean alkyl and alkoxy groups respectively which contain from 1 to 4 carbon atoms.

The thiocyanato group in the compounds of formula (I) may, in general, be introduced by diazotisation of a 1-naphthylamine of the formula:

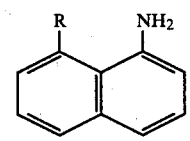

followed by reaction of the diazonium compound with an alkali metal thiocyanate, e.g. potassium thiocyanate, optionally together with a transition metal thiocyanate, e.g. cuprous thiocyanate. The amino group may be introduced into the 1-position of the naphthalene nucleaus in a protected form to allow subsequent introduction of the group R into the 8- position, the protecting group then being removed to liberate the free amino group which is then replaced by the thiocyanato group as indicated previously. Alternatively, the group R may be present in the naphthalene nucleus before introduction of a protected amino group or other group which is ultimately replaced by the thiocyanato group. Also compounds of the formula:

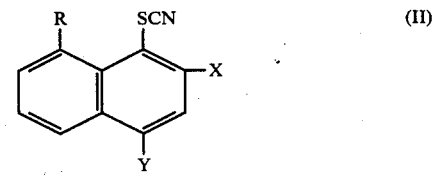

wherein R has the meaning defined above, and X and Y each independently represent a hydrogen atom or a group as defined for R, and wherein R, X and Y may be the same or different, provided that X and Y are not both hydrogen atoms, may be obtained by the reaction of a compound of the formula:

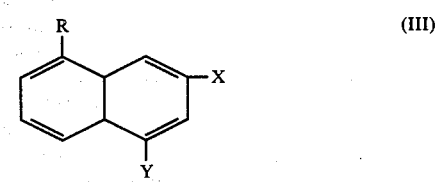

wherein R, X and Y have the meanings defined above, with thiocyanogen. The thiocyanogen may either be made in situ, for example, by stirring the naphthalene compound of formula (III) with an inorganic thiocyanate and an inert solvent at a temperature below 20° C. and adding bromine dropwise to the mixture, or by adding a previously prepared solution of thiocyanogen, for example, in carbon tetrachloride, to the naphthalene compound at a temperature below 20° C.

Other compounds of formula (I) within the scope of the invention may be obtained by conventional methods of organic chemistry. For example, halogen atoms may be introduced by diazotisation of an appropriate amino derivative followed by application of the Sandmeyer reaction. In this way 1-iodo-5-nitro-4-thiocyanatonaphthalene may be prepared from 1-amino-5-nitro-4-thiocyanatonaphthalene. Elimination of the amino group from the latter compound via its diazonium derivative gives 1-nitro-8-thiocyanatonaphthalene, which may also be prepared by diazotisation of 1-amino-8-nitronaphthalene followed by reaction with an alkali metal thiocyanate. Similarly, 1-amino-8-chloronaphthalene gives 1-chloro-8-thiocyanatonaphthalene. Acylamino derivatives may be obtained by acylation of the corresponding amino compounds. Thus, reaction of 1-amino-5-nitro-4-thiocyanatonaphthalene with acetic anhydride in acetic acid gives the 1-acetylamino derivative. 1-Amino-5-nitro-4-thiocyanatonaphthalene may itself be obtained by direct thiocyanation of 1-amino-5-nitronaphthalene; bis-thiocyanation gives 1-amino-2,4-dithiocyanato-5-nitronaphthalene, which may be converted into 2-amino-6-nitro-5-thiocyanatonaphtho[1,2-d]thiazole by refluxing in an alcoholic solvent containing a small quantity of a mineral acid. Likewise, thiocyanation of 1-amino-5-cyanonaphthalene gives 1-amino-5-cyano-4-thiocyanatonaphthalene; diamination of this compound via its diazonium derivative yields 1-cyano-8-thiocyanatonaphthalene.

The compounds of formula (I) above are valuable biocides, and according to a further feature of the invention there is provided a method for protecting a medium which is susceptible at attack by micro-organisms against such attack, and contolling or preventing the proliferation of micro-organisms in a medium already infected thereby, which comprises adding to the said medium a biocidal amount of a 1-thiocyanato-8-substituted naphthalene compound as hereinbefore defined.

In the above definition, preventing the proliferation of micro-organisms means that the micro-organisms are not allowed to multiply further, the number of micro-organisms not necessarily being substantially altered. Controlling the proliferation of micro-organisms means that the rate of multiplication of the micro-organisms is either reduced or rendered negative (i.e. a reduction in numbers, including the case of complete eradication).

The biocides of the invention are particularly useful in controlling the growth of bacteria, fungi and algae in aqueous media, as hereinbefore defined, but they also find application as paint film fungicides and algicides; in the prevention of fungal and/or bacterial attack on wood, hides and leather and for the in-can preservation of water-based paints and adhesives.

Preferred biocidal compounds within the scope of the present invention are 1-thiocyanato-8-nitronaphthalene and 1-acetylamino-5-nitro-4-thiocyanatonaphthalene, because of their greater effectiveness against a broad spectrum of micro-organisms.

The amount of biocide which is used will depend upon the medium which is being treated and the nature of the microorganisms involved, but for aqueous media an amount from 1 to 1000 parts per million by weight, based on the weight of the medium, may be used, from 25 to 500 parts per million by weight being generally effective, including the case in which the aqueous medium is a water-based paint.

When used as a paint film fungicide or algicide the biocide will generally be used in an amount to provide a concentration in the paint, before its application to a substrate, of from 500 to 10,000 parts per million by weight, based on the weight of the paint.

The biocidal compound of formula (I) may be added to the appropriate medium as the undiluted solid compound, as a solution in an organic solvent, for example, a lower alcohol such as methanol or ethanol, or dimethylformamide, if desired together with water, or as a dispersion in water prepared with the said of a dispersing agent, for example, the sodium salt of a naphthalene-2-sulphonic acid/formaldehyde condensate.

The method according to the present invention is particularly useful when the medium to be protected against infection by micro-organisms is a metal-working fluid comprising a stabilised oil-in-water emulsion or a synthetic metal-working fluid, a paint film or water-based paint, and infection-susceptible media protected against infection by micro-organisms by having incorporated therein a biocidal amount of a 1-thiocyanato-8-substituted naphthalene compound as hereinbefore defined constitute a further feature of the invention.

The invention is illustrated but not limited by the following Examples in which parts and percentages are by weight, and ppm means parts per million.

EXAMPLE 1

Preparation of 1-amino-5-nitro-4-thiocyanatonaphthalene 61.85 Parts of lead thiocyanate and 395 parts of methanol were stirred at 10° C. and a solution of 25.53 parts of bromine in 158 parts of methanol was added to the suspension, maintaining the temperature at 5°–12° C. The thiocyanogen liquors so obtained were filtered from the lead salts. The thiocyanogen filtrate was kept at 5°–15° C.

25 Parts of 1-amino-5-nitronaphthalene and 790 parts of methanol were stirred, heated to reflux and filtered hot from a small amount of impurity. The filtrate was cooled to 10° C.

The cold thiocyanogen solution was added to the stirred solution of 1-amino-5-nitronaphthalene, maintaining the temperature at 5°–15° C. The mixture was stirred a further one hour at 5°–15° C. and then made just alkaline (pH 7–8) by addition of concentrated ammonium hydroxide solution. The reaction mixture, after filtering from a small amount of insoluble material, was evaporated to dryness. The solid obtained was stirred with water, filtered, washed and dried.

The crude product was recrystallised from toluene (using charcoal). The yield of fairly pure product was 17.8 g, m.pt 155° C.

An analytically pure sample was obtained by repeated recrystallisations from toluene and had m.pt 162° C. The I.R. spectrum contained a band at 2150 cm$^{-1}$ due to thiocyanate group and bands at 3495 cm$^{-1}$, 3390 cm$^{-1}$ and 3240 cm$^{-1}$ due to a primary aromatic amine group.

Analysis, Found: C, 54.0; H, 3.1; N, 17.6; S, 13.6%; $C_{11}H_7N_3O_2S$ requires C, 53.9; H, 2.9; N, 17.1; S, 13.1%.

EXAMPLE 2

Preparation of 1-nitro-8-thiocyanatonaphthalene 24.5 Parts of 1-amino-5-nitro-4-thiocyanatonaphthalene (prepared as described above) were stirred with 524 parts glacial acetic acid at 65° C. and alowed to cool to room temperature. The suspension was then added slowly to a well stirred solution of nitrosyl sulphuric acid, (previously prepared from 13.8 parts sodium nitrite and 147 parts of concentrated sulphuric acid) maintaining the temperature at 16°–20° C. After the completion of the addition, the diazo solution was allowed to stir for a further 30 minutes.

28.6 Parts of cuprous oxide and 789 parts of ethanol were vigorously stirred at 55° C. and the above diazo solution was added slowly, maintaining the temperature at 55°–60° C. The reaction mixture was then cooled, filtered and washed. The filtrates and washings are combined and drowned out in 10,000 parts water.

The suspension was then filtered and washed well. The crude product was recrystallised from ethanol (using charcoal) to yield 9.2 g product m.pt 118°–119° C. The I.R. spectrum contained a thiocyanate band at 2160 cm$^{-1}$.

Analysis, Found: C, 57.9; H, 2.4; N, 12.2%. $C_{11}H_6N_2O_2S$ requires C, 57.4; H, 2.6; N, 12.2%. (N.B. a sample prepared from 1-amino-8-nitronaphthalene by diazotisation and reaction with inorganic thiocyanates gave a product with the same physical properties as above.

EXAMPLE 3

Preparation of 1-acetylamino-5-nitro-4-thiocyanatonaphthalene 24.5 parts of 1-amino-5-nitro-4-thiocyanatonaphthalene (prepared as described in Example 1) were stirred with 200 parts of acetic acid and 200 parts of acetic anhydride at room temperature for 16 hours. After drowning out the reaction mixture into water, the crude product was collected and recrystallised from ethanol.

Yield 2 g, m.pt 215°–216° C.

The I.R. spectrum contained a thiocyanate band at 2150 cm$^{-1}$ and bands at 3290 cm$^{-1}$ and 1660 cm$^{-1}$ duo to an amide group.

Analysis, Found: C, 55.1; H, 3.1; N, 14.7%; $C_{13}H_9N_3O_3S$ requires C, 54.4; H, 3.1; N, 14.6%.

EXAMPLE 4

Preparation of 1-iodo-5-nitro-4-thiocyanatonaphthalene

A solution of 2.45 parts of 1-amino-5-nitro-4-thiocyanatonaphthalene in 50 parts of glacial acetic acid was diazotised with a solution of nitrosylsulphuric acid, (previously prepared from 1.38 parts of sodium nitrite and 16 parts of concentrated sulphuric acid) maintaining the temperature at 16°–20° C. The diazo solution was then added to a solution of 3 parts of potassium iodide in 20 parts of water and allowed to stir for a further half hour. The crude product was filtered off, washed well, dried and recrystallised several times from ethanol to yield 0.5 g product, m.pt 181°–182° C. The I.R. spectrum contained a thiocyanate band at 2160 cm$^{-1}$.

Analysis, Found: C, 37.1; H, 1.4; N, 7.7%; $C_{11}H_5N_2O_2SI$ requires C, 37.1; H, 1.4; N, 7.9%

EXAMPLE 5

Preparation of 1-cyano-8-thiocyanatonaphthalene

This compound was prepared by thiocyanation of 4.18 parts of 1-amino-5-cyanonaphthalene, in a manner similar to that used to prepare 1-amino-5-nitro-4-thiocyanatonaphthalene in Exmaple 1, to yield 3.4 parts of crude 1-amino-5-cyano-4-thiocyanatonaphthelene.

3.4 Parts of impure 1-amino-5-cyano-4-thiocyanatonaphthelene were then deaminated by the method described in Example 2 for deamination of 1-amino-5-nitro-4-thiocyanatonaphthalene. The crude product, after drowning out into water, was filtered off, washed well, dried and recrystallised from ethanol to yield 0.62 parts of pure 1-cyano-8-thiocyanatonaphthalene, m.pt 129.5°–130.5° C. The I.R. spectrum contained a band at 2220 cm$^{-1}$ due to the cyano group and a band at 2160 cm$^{-1}$ due to the thiocyanate group.

Analysis, Found: C, 60.0; H, 2.7; N, 13.0%; $C_{12}H_6N_2S$ requires C, 68.6; H, 2.9; 13.3%.

EXAMPLE 6

Preparation of 1-chloro-8-thiocyanatonaphthalene 3.92 parts 8-chloro-1-naphthylamine were stirred in dilute hydrochloric at room temperature and diazotised by the careful addition of a solution of 1.52 parts sodium nitrite in water. The diazo solution was then added, at 10° C., to a stirred suspension of 3.5 parts potassium thiocyanate, 4.5 parts cuprous thiocyanate and 0.1 parts ferrous sulphate in water. After stirring the mixture for several hours, the product was filtered off and recrystallised several times from ethanol to yield 1 part of pure product, m.pt 77°–8° C. The I.R. spectrum contained a band at 2160 cm$^{-1}$ due to the thiocyanate group.

Analysis, Found: C, 60.1; H, 2.8; N, 6.3; Cl, 16.1%; $C_{11}H_6ClNS$ requires C, 60.1; H, 2.7; N, 6.4; Cl, 16.2%

EXAMPLE 7

Preparation of 1-amino-2,4-dithiocyanato-5-nitronaphthalene

A solution of 9.4 parts of 1-amino-5-nitronaphthalene in 300 parts of glacial acetic acid was treated at 16°–18° C. with a cold solution of thiocyanogen previously prepared by adding 16.8 parts of bromine in 70 parts of acetic acid to 37.2 parts of lead thiocyanate in 160 parts of acetic acid.

The reaction mixture was poured into ice/water and the crude product was filtered off. After several crystallisations from ethanol, the product was finally recrystallised from aqueous acetone. Yield 3 g, m.pt>250° C. The I.R. spectrum contained bands at 3460 cm$^{-1}$ and 3360 cm$^{-1}$ due to the amino group and bands at 2150 cm$^{-1}$ and 2160 cm$^{-1}$ due to the thiocyanate groups.

Analysis, Found; C, 48.7; H, 2.0; N, 18.2%. $C_{12}H_6N_4O_2S_2$ requires C, 47.7; H, 2.0; N, 18.5%.

EXAMPLE 8

Preparation of 2-amino-6-nitro-5-thiocyanato[1,2-d]thiazole 0.25 Parts of 1-amino-2,4-dithiocyanto-5-nitronaphthalene were heated in 25 parts of refluxing isopropanol containing 0.1 parts of concentrated hydrochloric acid for eighteen hours. The suspension was drowned out into 250 parts of ice/water. The essentially pure product was filtered off, washed and dried. Yield 0.22 parts, m.pt >285° C. The I.R. spectrum contained bands at 3360 cm$^{-1}$, 3310 cm$^{-1}$, 3110 cm$^{-1}$ and 1650 cm$^{-1}$ due to a 2-aminothiazole ring, and a band at 2160 cm$^{-1}$ due to one thiocyanate group.

Analysis, Found C, 47.2; H, 1.9; N, 17.1; S, 20.9%; $C_{12}H_6N_4O_2S_2$ requires C, 47.7; H, 2.0; N, 18.5; S, 21.2%.

EXAMPLE 9

In Vitro Bacteriostatic and Fungistatic Activity in Agar

1-Nitro-8-thiocyanatonaphthalene was dissolved in dimethyl formamide (DMF) (0.1 g/10 ml solvent) and added to nutrient agar to give a concentration of 100 ppm, and to malt agar to give concentrations of 100, 20 and 10 ppm. The control consisted of malt and nutrient agars containing 1 ml DMF per 100 ml agar (i.e. the level of DMF in the 100 ppm biocide treatment). The molten biocide-containing and control media were poured into Petri dishes and allowed to solidify. Petri dishes containing each biocide concentration were poured in triplicate.

A Microtiter AM 80 Automatic Inoculator was used for inoculating the plates. Nutrient agar plates were inoculated with the bacteria *Pseudomonas aeruginosa, Escherichia coli,* and *Staphylococcus aureus,* and the malt agar plates were inoculated with the fungi, *Pullularia pullulans, Aspergillus niger, Cladosporium sphaerospermum, Alternaria tenuis,* and *Chaetomium globosum.*

The nutrient agar plates were incubated at 37° C. for 24 hours and malt agar plates were incubated at 25° C. for 48 hours, after which the plates were examined for the presence or absence of microbial growth.

| Concentration of Biocide | Results Growth of | | | | | | | |
|---|---|---|---|---|---|---|---|---|
| | *Ps. aerug* | *E. coli* | *S aureus* | *P. pullulans* | *Asp. niger* | *Clad sphaer* | *Alt. tenuis* | *Chaet. globosum* |
| 100 ppm | − | − | − | − | − | − | − | − |
| 20 ppm | } NOT TESTED | | | − | − | − | − | − |
| 10 ppm | | | | − | − | − | − | − |
| Control | + | + | + | + | + | + | + | + |

+, = Growth, i.e. organism not inhibited
−, = no growth i.e. growth totally inhibited These results show that 1-nitro-8-thiocyanatonaphthalene has both antifungal and antibacterial activity.

EXAMPLE 10

Determination of Bactericidal Activity of 1-Nitro-8-thiocyanatonaphthalene

Preparation of Reaction Mixture

A 1% solution of the biocide was prepared by adding 0.1 g 1-nitro-8-thiocyanatonaphthalene to 10 ml DMF. One-ml, 0.5 ml, 0.25 ml and 0.1 ml portions of the 1% solution were added to 100-ml volumes of sterile deionised water in 250-ml sterile cotton-wool plugged conical flasks to give final concentrations of 100, 50, 25 and 10 ppm of biocide. The control flask consisted of 100 ml water to which 1 ml of DMF had been added.

Preparation of Inoculum

An 18-hour broth culture of *Pseudomonas aeruginosa* was prepared by transferring one loop-full of a 24-hour broth culture into 100 ml of nutrient broth in a 250-ml conical flask and incubating the latter in an orbital shaker at 37° C. The 18-hour culture was diluted 1 in 10 in sterile deionised water and 1 ml of the latter suspension was used as the inoculum.

Inoculation and Incubation of Reaction Mixture

One ml of the inoculum was added to the 100-ml volumes of biocide solutions, and the latter were incubated statically at room temperature.

Determination of Survivors

Samples were removed from the biocide solutions after contact periods of 2, 4 and 6 hours, and after decimal dilution of the samples in physiological saline, survivors were determined in nutrient agar (2 days at 37° C.).

| Concentration of Biocide | Results Survivors (cells/ml) after contact times of | | |
|---|---|---|---|
| | 2 hours | 4 hours | 6 hours |
| 100 ppm | <10 | <10 | <10 |
| 50 ppm | <10 | <10 | <10 |
| 25 ppm | <10 | <10 | <10 |
| 10 ppm | 2.0 × 10$^1$ | <10 | <10 |
| Control | 2.9 × 10$^6$ | 3.6 × 10$^6$ | 7.1 × 10$^6$ |

These results show that 1-nitro-8-thiocyanatonaphthalene is an active bactericidal agent.

EXAMPLE 13

Determination of the Ability of 1-Nitro-8-thiocyanatonaphthalene to Withstand Several Challenges of Bacteria Nutrient broth was prepared in sterile test-tubes containing 5, 10, 25, 50, 75 and 100 ppm of 1-nitro-8-thiocyanatonaphthalene. The biocide was prepared in solution 20 times as strong as the above-mentioned concentrations, so that 1 ml of the biocide solutions added to 19 ml of nutrient broth gave the required final concentrations. The control consisted of nutrient broth with no biocide. Each concentration of biocide and the control was set up in triplicate. Each nutrient broth tube was inoculated with 0.1 ml of a 24 hour broth culture of *Pseudomonas aeruginosa* and the inoculated broths were incubated at 37° C. for 24 hours, after which the tubes were examined for the presence or absence of growth before the second inoculation was made. Altogether the tubes were inoculated four times.

| Concentration of Biocide | Results Presence or Absence of Growth after | | | |
|---|---|---|---|---|
| | 1st Inoculation | 2nd Inoculation | 3rd Inoculation | 4th Inoculation |
| 100 ppm | − − − | − − − | − − − | − − − |
| 75 ppm | − − − | − − − | − − − | − − − |
| 50 ppm | − − − | − − − | + + + | + + + |

-continued

| Concen- | Results Presence or Absence of Growth after | | | |
|---|---|---|---|---|
| tration of Biocide | 1st Inoculation | 2nd Inoculation | 3rd Inoculation | 4th Inoculation |
| 25 ppm | − − − | − − − | + + + | + + + |
| 10 ppm | − − − | + + + | + + + | + + + |
| 5 ppm | + + + | + + + | + + + | + + + |
| Control (no biocide) | + + + | + + + | + + + | + + + |

The results show that the higher levels of 1-nitro-8-thiocyanatonaphthalene (e.g. the 100 ppm level) control at least four bacterial challenges. The chemical is therefore a stable antibacterial agent with high activity.

EXAMPLE 12

Comparison of the In-Vitro Fungicidal Activities of 1-Nitro-8-thiocyanatonaphthalene Preparation of Reaction Mixture A 1% solution was prepared by dissolving 0.1 g of the solid compound in 10 ml DMF. 0.5-ml and 0.1-ml volumes of the above-mentioned 1% solutions were added to 100 ml volumes of sterile deionised water in sterile cotton wool plugged 250-ml conical flasks to give solutions of 50 and 100 ppm biocide. The control flask consisted of 100 ml water.

Preparation of Inoculum 1 cm-diameter discs were cut from cloth and transferred into water in a conical flask, and sterilised by autoclaving for 15 minutes, at 15 p.s.i. The discs were then transferred onto malt agar in Petri dishes (6 per Petri dish) and inoculated with a spore suspension of *Aspergillus niger* by spraying the plate and contents from an atomiser. The inoculated discs were incubated for 24 hours at 25° C., after which time they were overgrown with mycelium but there were no spores present.

Inoculation and Incubation of Reaction Mixture

All reaction mixtures were maintained at 30° C. in an orbital shaker. At zero time six fungus-impregnated discs were transferred into each flask.

Determination of Survivors

After contact periods of 3, 6 and 24 hours two of the discs were removed from each flask and transferred into 100 ml of sterile water in a sterile bottle. The latter was momentarily shaken and after a 30-minute period the two discs were removed from the water and transferred on to malt agar in a Petri dish. All Petri dishes containing the fungus-impregnated discs which had been subjected to biocide treatment were incubated for 3 days at 25° C. The plates were examined for the presence or absence of fungal growth. The presence of fungal growth indicates that the biocide treatment had not totally killed the mycelium on the discs, whereas the absence of growth indicated total kill by the biocide treatment.

| Concen- | Results Survival of fungi in biocide solutions after | | | | | |
|---|---|---|---|---|---|---|
| tration of | 3 hours | | 6 hours | | 24 hours | |
| Biocide | Repl.1 | Repl.2 | Repl.1 | Repl.2 | Repl.1 | Repl.2 |
| 100 ppm | 3 | 3 | 1 | 0 | 0 | 0 |
| 50 ppm | 3 | 3 | 3 | 3 | 0 | 0 |
| Control | 3 | 3 | 3 | 3 | 3 | 3 |

In the above Table: -
3 fungal growth over entire disc and readily spreading over surrounding agar (i.e. no kill).
2 fungal growth essentially confined to the disc.
1 fungal growth over up to half of the area of the disc only (partial kill)
0 no fungal growth on disc (i.e. total kill).

The results show that 1-nitro-8-thiocyanatonaphthalene has fungicidal activity.

EXAMPLE 13

Activity of 1-Nitro-8-thiocyanatonaphthalene in Controlling Bacterial Growth in Metal-Working Fluids The biocide, in the form of a 1% solution in DMF, was added to 100 ml volumes of a 1 in 20 oil in water emulsion prepared from Prosol 44 emulsifiable oil (Mobil) to give final concentrations of 50, 100 and 200 ppm in the emulsion.

The biocide-containing emulsions and biocide-free controls in 250 ml cotton-wool plugged conical flasks were incubated at 30° C. on a rotary shaker. The emulsions were inoculated once weekly with 0.5 ml of an overnight broth culture of *Pesudomonas aeruginosa* and survivors were determined after 1 and 3 days in each week. Survivors were determined in nutrient agar by decimal dilution of 1 ml samples, removed from the emulsions.

| | Results Survivors (cells/ml) in | | | |
|---|---|---|---|---|
| Concentration | Week 1 | | Week 2 | |
| of Biocide | Day 1 | Day 3 | Day 1 | Day 3 |
| 50 ppm | <10 | $1.2 \times 10^2$ | $9.6 \times 10^4$ | $>3.0 \times 10^5$ |
| 100 ppm | <10 | <10 | <10 | <10 |
| 200 ppm | <10 | <10 | <10 | <10 |
| Control | $7.1 \times 10^6$ | $6.2 \times 10^7$ | $6.1 \times 10^7$ | $6.7 \times 10^7$ |

The results indicate that 1-nitro-8-thiocyanatonaphthalene has high antibacterial activity in an oil-in-water emulsion.

EXAMPLE 14

Activity of 1-nitro-8-thiocyanatonaphthalene as a Paint Film Fungicide Incorporation of Biocide into Paint A 0.09 g quantity of the biocide was added to 18.9 g mill base, and mixed thoroughly by using a high speed micro shear stirrer. 11.1 g of PVA copolymer emulsion was then slowly stirred into the biocide-containing mill base by hand. The biocide was therefore present in the final emulsion paint at a concentration of 3000 ppm. The paint sample was then stored in a tightly-sealed plastic container at 50° C. for 2 weeks. The control consisted of paint containing no biocide.

Application of Biocide-Containing Paint on Filter Paper and Subsequent Treatment Two coats of paint were applied by brush to one side of two 7-cm diameter Whatman No. 1 filter papers, allowing 24 hours for drying between coats. The filter papers were placed in an oven at 50° C. for 24 hours and then transferred to a leaching apparatus for 24 hours in which a fine mist of water was sprayed over the filter papers.

The weathered filter papers were then ethylene oxide sterilised, after which they were transferred on to malt agar in a Petri dish. For each paint variant one filter paper was inoculated with a spore suspension of *Alternaria tenuis* and the second filter paper was inoculated with a *Cladosporium sphaerospermum* spore suspension. The inoculated Petri dishes were then incubated for 5 days at 25° C., after which the filter papers were examined for the presence or absence of growth.

| Results Growth on Filter Paper of:- | | |
|---|---|---|
|  | Alternaria tenuis | Cladosporium sphaerospermum |
| Biocide | 0 | 0 |
| Control | 3 | 2 |

3 = Growth over the entire surface of the filter paper
2 = Growth over 50% of the filter paper
0 = No growth; i.e. total inhibition of fungal growth by the biocide.

The results show that 1-nitro-8-thiocyanatonaphthalene has high activity as a paint film fungicide.

EXAMPLE 15

The procedure described in Example 9 was repeated, comparing the following thiocyanatonaphthalenes for antibacterial and antifungal activity:
A. 1-Nitro-8-thiocyanatonaphthalene
B. 1-Acetylamino-5-nitro-4-thiocyanatonaphthalene
C. 1-Chloro-8-thiocyanatonaphthalene
D. 1-Amino-5-nitro-4-thiocyanatonaphthalene
E. 1-Iodo-5-nitro-4-thiocyanatonaphthalene
F. 1-Amino-2,4-bis(thiocyanato)-5-nitronaphthalene
G. 2-Amino-6-nitro-5-thiocyanatonaphtho[1,2-d]thiazole
H. 1-Cyano-8-thiocyanatonaphthalene
The following results were obtained:

| Biocide | Concentration (ppm) | Growth of | | | | | | | |
|---|---|---|---|---|---|---|---|---|---|
|  |  | Ps. aerug | E. coli | S. aureus | P. pullulans | Asp. niger | Clad. sphaer | Alt. tenuis | Chaet. globosum |
| A | 100 | − | − | − | − | − | − | − | − |
| B | 100 | − | − | − | − | − | − | NT | − |
| C | 100 | + | + | + | − | + | + | NT | + |
| D | 100 | + | + | + | − | + | − | − | + |
| E | 100 | − | − | + | − | − | − | − | − |
| F | 100 | − | + | + | − | − | + | − | − |
| G | 200 | + | + | + | + | + | − | − | − |
| H | 200 | + | + | + | − | + | − | − | − |
| Control (no biocide) |  | + | + | + | + | + | + | + | + |

In the above table − and + mean the absence or presence, respectively, of bacterial or fungal growth.

From these results it can be seen that compounds A, B and E have a broad spectrum of activity against both bacteria and fungi, whilst the remaining compounds have antifungal rather than antibacterial activity, although F is active against Ps.aeruginosa.

EXAMPLE 16

Bactericidal Activity of
1-Nitro-8-thiocyanatonaphthalene (A) and
1-Acetylamino-5-nitro-4-thiocyanatonaphthalene (B) in
a Cooling Tower Water An artificial cooling tower water was prepared from:

| Solution 1: | Calcium chloride | 10.769 g |
|---|---|---|
|  | Magnesium chloride | 6.782 g |
|  | Water | 100 ml |
| and Solution 2: | Sodium bicarbonate | 5.603 g |
|  | Water | 100 ml | by mixing 4 ml of Solution 1, 8 ml of Solution 2 and 2 ml of ethylene glycol and making the mixture up to 2 liters with distilled water. The solution was transferred in 100 ml portions into bottles, and autoclaved to sterilise the bottles and contents. The pH of the solution was 8.5.

The test chemicals A and B, as 1% solutions in dimethylformamide, were added to 100 ml volumes of the artificial cooling tower water in 250 ml sterile conical flasks plugged with cotton wool, to give concentrations of active ingredient of 50 and 100 ppm. The control consisted of cooling tower water with no biocide.

The flasks were transferred to an orbital shaker at 30° C. and, after a 30 minute equilibration period, were inoculated with 1 ml of an 18 hour broth culture of *Pseudomonas aeruginosa*.

After incubation periods of 1, 2 and 4 hours one-ml volumes were removed from each flask, decimally diluted in physiological saline, and surviving bacteria were determined on nutrient agar. After incubation of the nutrient agar plates for 2 days at 37° C., the surviving bacteria were enumerated.

Results were as follows:

| Treatment | | Survivors (cells/ml) after: | | |
|---|---|---|---|---|
|  |  | 1 hour | 2 hours | 4 hours |
| Compound A, | 200 ppm | <10 | <10 | <10 |
|  | 100 ppm | <10 | <10 | <10 |
|  | 50 ppm | <10 | <10 | <10 |
| Compound B, | 200 ppm | $2.0 \times 10^4$ | <10 | <10 |
|  | 100 ppm | $6.0 \times 10^4$ | <10 | <10 |
|  | 50 ppm | $5.0 \times 10^4$ | <10 | <10 |
| Control |  | $3.0 \times 10^8$ |  | $2.5 \times 10^8$ |

These results show that Compounds A and B have high activity as cooling tower water biocides.

EXAMPLE 17

Bactericidal Activity of
1-Nitro-8-thiocyanatonaphthalene (A) and
1-Acetylamino-5-nitro-4-thiocyanatonaphthalene (B) in Paper Mill Water An artificial paper mill "white water" was prepared having the following composition:

| | |
|---|---|
| Starch | 0.035 g |
| Clay | 0.035 g |
| Titanium dioxide | 0.023 g |
| Animal glue | 0.001 g |
| Kymine resin | 0.034 g |
| Sodium aluminate | 0.023 g |
| Rosin size | 0.023 g |
| Glucose | 2.84 g |
| Peptone | 1.5 g |
| 10% ground wood pulp* | 37 ml |
| Water to | 1 liter |

*10 g dry wood in 100 g suspension

This medium was dispensed in 100 ml volumes, autoclaved at 1.05 kg/cm² for 15 minutes and transferred into 250 ml sterile conical flasks.

The test chemicals A and B as 1% solutions in dimethylformamide were added to 100 ml volumes of white water medium to give concentrations of active ingredient of 50 and 100 ppm, 1 ml of an 18 hour culture of *Enterobacter cloacae* was added, and the inoculated media were incubated in 250 ml flasks in a shaking water bath at 30° C. The control consisted of the white water medium without biocide.

After incubation periods of 1,2 and 4 hours, one-ml volumes were removed from each flask, decimally diluted in physiological saline, and surviving bacteria were determined on nutrient agar. After incubation of the nutrient agar plates for 2 days at 37° C. the surviving bacteria were enumerated.

Results were as follows:

| Treatment | | Survivors (cells/ml) after | | |
|---|---|---|---|---|
| | | 1 hour | 2 hours | 4 hours |
| Compound A, | 50 ppm | <10 | <10 | <10 |
| | 100 ppm | $1.2 \times 10^2$ | $6.6 \times 10^2$ | <10 |
| Compound B, | 50 ppm | $4.2 \times 10^3$ | $2.3 \times 10^2$ | $8.1 \times 10^3$ |
| | 100 ppm | $5.6 \times 10^3$ | $4.0 \times 10^3$ | $3.9 \times 10^2$ |
| Control | | $4.1 \times 10^7$ | $5.6 \times 10^7$ | $8.2 \times 10^7$ |

These results show that Compounds A and B have both markedly reduced the bacterial count and are effective biocides in paper mill water.

EXAMPLE 18

Antibacterial Activity of
1-Nitro-8-thiocyanatonaphthalene (A) in Oil Recovery Water An artificial oil recovery water (see water medium) having the following composition was prepared:

| | |
|---|---|
| Dipotassium hydrogen phosphate | 0.5 g |
| Ammonium chloride | 1.0 g |
| Sodium sulphate | 1.0 g |
| Sodium lactate (70%) | 5.0 ml |
| Yeast extract | 1.0 g |
| Sodium ascorbate | 0.1 g |
| Sodium thioglycollate | 0.1 g |
| Ferrous sulphate | 0.5 g |
| Aged sea water* | to 1 liter |

*75% sea water; 25% distilled water. The sea water was previously aged by storage in the dark for 1 month at room temperature.

This medium was dispensed in 18 ml volumes into screw capped bottles and autoclaved to sterilise the bottles and contents. After the autoclave treatment 1 ml of an aqueous solution of sodium sulphite was added to each bottle to give a finel concentration of 10 ppm.

Compound A and sterile distilled water were then added to give a final volume of 20 ml in each case, and concentrations of 5, 10 and 50 ppm of Compound A. The control consisted of the sea water medium and sodium sulphite, without biocide.

Each bottle containing 20 ml medium was inoculated with 0.2 ml Desulphovibrio sp. and incubated for 5 days at 25° C., after which the media were examined for the presence or absence of bacterial growth. Each test was carried out in triplicate.

Results were as follows:

| Treatment | | Growth of Desulphovibrio |
|---|---|---|
| Compound A | 50 ppm | − − − |
| | 10 ppm | − − − |
| | 5 | + + + |
| Control | | + + + |

In the above table − and + mean the absence and presence of bacterial growth, respectively.

These results show that at a concentration of 10 ppm Compound A controls the growth of Desulphovibrio and has utility as a biocide in oil recovery water.

EXAMPLE 19

Antibacterial Activity of
1-Acetylamino-5-nitro-4-thiocyanatonaphthalene (B) as an In-Can Paint Preservative Compound B, as a 1% solution in dimethylformamide, was added to 50 g quantities of a styrene-acrylic emulsion paint to give final concentrations of 100 and 200 ppm. The control consisted of paint containing 1 ml of dimethylformamide (the amount required to provide the 200 ppm level of biocide concentration) but no biocide.

The paint samples were each inoculated with 0.5 ml of a mixture of overnight broth cultures of *Ps. aeruginosa, E. coli* and *Enterobacter cloacae* once weekly for 2 weeks. Surviving bacteria were determined each week, 1 and 3 days after inoculation, in nutrient agar by the decimal dilution method.

Results were as follows:

| Treatment | | Survivors (cells/g paint) in | | | |
|---|---|---|---|---|---|
| | | Week 1 | | Week 2 | |
| | | Day 1 | Day 3 | Day 1 | Day 3 |
| Compound B | 200 ppm | <10 | <10 | <10 | <10 |
| | 100 ppm | $5.6 \times 10^5$ | $1.0 \times 10^5$ | $7.0 \times 10^4$ | $3.0 \times 10^4$ |
| Control | | $5.9 \times 10^6$ | $2.0 \times 10^7$ | $2.5 \times 10^7$ | $4.0 \times 10^6$ |

These results show that at a level of 200 ppm Compound B has high activity as an in-can paint preservative.

EXAMPLE 20

Activity of 1-Acetylamino-5-nitro-4-thiocyanatonaphthalene (B) as a Metal Working Fluid Biocide Compound B, as a 1% solution in dimethylformamide, was added to 100 ml volumes of a 5% oil-in-water emulsion prepared from Prosol 44 (Mobil) emulsifiable oil, to give final concentrations of 100 and 200 ppm of active ingredient. The control consisted of 2 ml of dimethylformamide in 100 ml of the emulsion (i.e. the amount of dimethylformamide added to the emulsion to give the 200 ppm concentration of biocide).

The 100 ml volumes of emulsion in 250 ml conical flasks plugged with cotton wool were inoculated with 0.5 ml of an 18 hour broth culture of *Pseudomonas aeruginosa*, transferred to an orbital shaker and incubated at 30° C. The test emulsions were inoculated once weekly for 3 weeks. Surviving bacteria were determined on nutrient agar by the decimal dilution procedure after incubation periods of 1 and 3 days in each week.

Results were as follows:

| Treatment | | Survivors (cells/ml) after | | | | | |
|---|---|---|---|---|---|---|---|
| | | Week 1 | | Week 2 | | Week 3 | |
| | | Day 1 | Day 3 | Day 1 | Day 3 | Day 1 | Day 3 |
| Compound B | 100 ppm | <10 | <10 | <10 | <10 | $3.9 \times 10^4$ | <10 |
| | 200 ppm | <10 | <10 | <10 | <10 | <10 | <10 |
| Control | | $1.64 \times 10^6$ | $1.54 \times 10^7$ | $8.9 \times 10^7$ | $1.30 \times 10^8$ | $>2.0 \times 10^8$ | $2.8 \times 10^8$ |

These results show that Compound B is highly active as a metal working fluid biocide.

EXAMPLE 21

Algicidal Activity of 1-Nitro-8-thiocyanatonaphthalene (A) and 1-Acetylamino-5-nitro-4-thiocyanatonaphthalene (B)

*Alkystrodesmus spirilliformis, Stichococcus bacillaris* and *Chlamydomonas reinhardii* were inoculated into one-litre batches of Difco algal broth and incubated at 15° C. for 2 weeks in an illuminated refrigerator. The three cultures were then combined and the mixed culture was dispensed in 50 ml volumes into 100 ml sterile conical flasks.

Compounds A and B were added to give final concentrations of 0.1, 0.5, 5.0 and 10.0 ppm.

The test samples were incubated for up to 2 weeks in the illuminated refrigerator at 15° C., and the flasks were examined for the presence or absence of a green colouration. The retention of the green colour indicated that the algae remained viable, whereas lack of colour of the sample indicated that the algae had been killed.

Results were as follows:

| Treatment | Minimum Lethan Concentration* (ppm) after | | |
|---|---|---|---|
| | 3 Days | 7 Days | 14 Days |
| Compound A | 1.0 | 0.1 | 0.1 |
| Compound B | >10 | 10 | 10 |

*i.e. the minimum concentration of biocide at which no green colouration was observed.

These results show that Compounds A and B both have antialgal activity.

We claim:

1. 1-Thiocyanato-8-substituted naphthalene compounds of the formula:

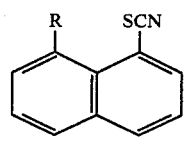

where R is alkyl, alkoxy, aryl, aryloxy, hydroxy, halogen, nitro, cyano, sulphonic acid, primary, secondary or tertiary amino, carbamoyl or sulphamoyl, and wherein the naphthalene nucleus may carry other substituents selected from the group consisting of lower alkyl, lower alkoxy, hydroxy, halogen, nitro, amino, acylamino, sulphonic acid, sulphamoyl and thiocyanato.

2. A naphthalene compound as claimed in claim 1 wherein R is selected from the group consisting of methyl, ethyl, n-propyl, isopropyl, n-butyl, 2-hydroxyethyl, 2-chloroethyl, 2-methoxyethyl, methoxy, ethoxy, phenyl and phenoxy groups.

3. Nitro-8-thiocyanatonaphthalene.

4. 1-Acetylamino-5-nitro-4-thiocyanatonaphthalene.

5. A biocidal 1-thiocyanato-8-substituted-naphthalene compound wherein the substitution in the 8-position is selected from the group consisting of alkyl, alkoxy, aryl, aryloxy, hydroxy, halogen, nitro, cyano, sulphonic acid, primary, secondary or tertiary amino, carbamoyl or sulphamoyl.

6. A method for protecting a medium which is susceptible to attack by micro-organisms against such attack, and controlling or preventing the proliferation of micro-organisms is a medium already infected thereby, which comprises adding to the medium a biocidal amount of a 1-thiocyanate-8-substituted naphthalene compound as claimed in claim 5.

7. A method as claimed in claim 6 wherein the medium is an aqueous medium, the thiocyanatonaphthalene compound being added in an amount from 1 to 1000 parts per million by weight, based on the weight of the medium.

8. A method as claimed in claim 7 wherein the thiocyanatonaphthalene compound is added in an amount from 25 to 500 parts per million by weight, based on the weight of the medium.

9. A method as claimed in claim 7 wherein the aqueous medium is a water-based paint, a metal-working fluid comprising a stabilised oil-in-water emulsion or a synthetic metal-working fluid.

10. A method as claimed in claim 6 wherein the medium is a paint film, the thiocyanatonaphthalene compound being used in an amount to provide a concentration in the paint, before its application to a substrate, of from 500 to 10,000 parts per million by weight, based on the weight of the paint.

11. A biocidal 1-thiocyanato-8-substituted-naphthalene compound according to claim 5 wherein alkyl is lower alkyl or substituted lower alkyl the substitution being selected from the group consisting of hydroxy, alkoxy and halogen, aryl is phenyl or substituted phenyl, the substitution being selected from alkyl, alkoxy, nitro and halogen, aryloxy is phenoxy or substituted phenoxy the substitution being selected from the group consisting of alkyl, alkoxy, nitro and halogen and the sulphamoyl and carbamoyl groups have the general formulae $-SO_2NR^1R^2$ and $-CONR^1R^2$ respectively wherein $R^1$ and $R^2$ are selected from the group consisting of hydrogen and hydrogen, hydrogen and lower alkyl, lower alkyl and lower alkyl and hydrogen and phenyl, or $R^1$ and $R^2$ together are selected from the group consisting of $-(CH_2)_5-$ and $-(CH_2)_2-O-(CH_2)_2-$.

12. A biocide according to claim 5 which is further substituted in the naphthalene ring in other than the 1 and 8 positions by at least one member of the group consisting of lower alkyl, lower alkoxy, hydroxy, halogen, nitro, amino, acylamino, sulphonic acid, sulphamoyl and thiocyanato.

* * * * *